US010258802B2

(12) United States Patent
Soltis et al.

(10) Patent No.: US 10,258,802 B2
(45) Date of Patent: Apr. 16, 2019

(54) DELIVERY DEVICES AND METHODS FOR LEADLESS CARDIAC DEVICES

(71) Applicant: CARDIAC PACEMAKERS, INC., St. Paul, MN (US)

(72) Inventors: Brian Soltis, St. Paul, MN (US); Kurt G. Koubal, Mound, MN (US); Benjamin J. Haasl, Forest Lake, MN (US); Ronald W. Kunkel, Jim Falls, WI (US); Brian L. Schmidt, White Bear Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 120 days.

(21) Appl. No.: 15/354,574

(22) Filed: Nov. 17, 2016

(65) Prior Publication Data

US 2017/0143980 A1 May 25, 2017

Related U.S. Application Data

(60) Provisional application No. 62/258,064, filed on Nov. 20, 2015.

(51) Int. Cl.
*A61N 1/00* (2006.01)
*A61N 1/375* (2006.01)
*A61N 1/05* (2006.01)
*A61B 17/34* (2006.01)
*A61N 1/372* (2006.01)

(52) U.S. Cl.
CPC ........ *A61N 1/3756* (2013.01); *A61B 17/3468* (2013.01); *A61N 1/0573* (2013.01); *A61N 1/37205* (2013.01)

(58) Field of Classification Search
USPC .................................................. 607/122, 126
See application file for complete search history.

(56) References Cited

U.S. PATENT DOCUMENTS

| | | | |
|---|---|---|---|
| 5,201,757 | A | 4/1993 | Heyn et al. |
| 5,433,723 | A | 7/1995 | Lindenberg et al. |
| 5,683,451 | A | 11/1997 | Lenker et al. |
| 5,749,921 | A | 5/1998 | Lenker et al. |
| 5,755,773 | A | 5/1998 | Evans et al. |
| 5,759,186 | A | 6/1998 | Bachmann et al. |
| 5,807,399 | A | 9/1998 | Laske et al. |
| 5,824,041 | A | 10/1998 | Lenker et al. |
| 5,868,755 | A | 2/1999 | Kanner et al. |
| 5,908,381 | A | 6/1999 | Aznoian et al. |

(Continued)

FOREIGN PATENT DOCUMENTS

| | | |
|---|---|---|
| DE | 9209908 U1 | 9/1992 |
| DE | 4323866 A1 | 1/1994 |

(Continued)

*Primary Examiner* — Nicole F Johnson
(74) *Attorney, Agent, or Firm* — Seager, Tufte & Wickhem LLP

(57) ABSTRACT

Delivery devices, systems, and methods for delivering implantable leadless pacing devices are disclosed. An example delivery system may comprise a delivery device, an implantable leadless pacing device, and a tether. The tether may be made of a material which allows for a lubricious, strong, no stretch, no memory tether. The tether may releasably secure the implantable leadless pacing device to the delivery device.

20 Claims, 16 Drawing Sheets

(56) References Cited

U.S. PATENT DOCUMENTS

| | | |
|---|---|---|
| 5,954,729 A | 9/1999 | Bachmann et al. |
| 6,143,021 A | 11/2000 | Staehle |
| 6,162,231 A | 11/2000 | Staehle |
| 6,391,051 B2 | 5/2002 | Sullivan, III et al. |
| 6,395,017 B1 | 5/2002 | Dwyer et al. |
| 6,409,674 B1 | 6/2002 | Brockway et al. |
| 6,413,269 B1 | 7/2002 | Bui et al. |
| 6,428,566 B1 | 8/2002 | Holt |
| 6,514,261 B1 | 2/2003 | Randall et al. |
| 6,582,441 B1 | 6/2003 | He et al. |
| 6,629,981 B2 | 10/2003 | Bui et al. |
| 6,638,268 B2 | 10/2003 | Niazi |
| 6,669,719 B2 | 12/2003 | Wallace et al. |
| 6,726,712 B1 | 4/2004 | Raeder-Devens et al. |
| 6,786,918 B1 | 9/2004 | Krivoruchko et al. |
| 6,866,669 B2 | 3/2005 | Buzzard et al. |
| 7,309,350 B2 | 12/2007 | Landreville et al. |
| 7,381,216 B2 | 6/2008 | Buzzard et al. |
| 7,393,357 B2 | 7/2008 | Stelter et al. |
| 7,608,099 B2 | 10/2009 | Johnson et al. |
| 7,731,654 B2 | 6/2010 | Mangiardi et al. |
| 7,799,037 B1 | 9/2010 | He et al. |
| 7,840,281 B2 | 11/2010 | Kveen et al. |
| 7,993,351 B2 | 8/2011 | Worley et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,439,934 B2 | 5/2013 | Satasiya et al. |
| 8,504,156 B2 | 8/2013 | Bonner et al. |
| 8,518,099 B2 | 8/2013 | Chanduszko et al. |
| 8,535,366 B2 | 9/2013 | Mangiardi et al. |
| 8,548,605 B2 | 10/2013 | Ollivier |
| 8,615,310 B2 | 12/2013 | Khairkhahan et al. |
| 8,634,912 B2 | 1/2014 | Bomzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,855,789 B2 | 10/2014 | Jacobson |
| 8,903,513 B2 | 12/2014 | Ollivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,958,892 B2 | 2/2015 | Khairkhahan et al. |
| 9,072,872 B2 | 7/2015 | Asleson et al. |
| 9,101,281 B2 | 8/2015 | Reinert et al. |
| 9,126,032 B2 | 9/2015 | Khairkhahan et al. |
| 9,168,372 B2 | 10/2015 | Fain |
| 9,205,225 B2 | 12/2015 | Khairkhahan et al. |
| 9,216,293 B2 | 12/2015 | Berthiaume et al. |
| 9,220,906 B2 | 12/2015 | Griswold |
| 9,238,145 B2 | 1/2016 | Wenzel et al. |
| 9,283,382 B2 | 3/2016 | Berthiaume et al. |
| 9,308,374 B2 | 4/2016 | Kveen et al. |
| 9,339,197 B2 | 5/2016 | Griswold et al. |
| 9,358,387 B2 | 6/2016 | Suwito et al. |
| 9,414,857 B2 | 8/2016 | Wood et al. |
| 9,446,248 B2 | 9/2016 | Sheldon et al. |
| 9,463,315 B2 | 10/2016 | Bornzin et al. |
| 9,468,773 B1 | 10/2016 | Anderson et al. |
| 9,526,522 B2 | 12/2016 | Wood et al. |
| 9,526,891 B2 | 12/2016 | Eggen et al. |
| 9,539,423 B2 | 1/2017 | Bonner et al. |
| 2001/0052345 A1 | 12/2001 | Niazi |
| 2002/0151967 A1 | 10/2002 | Mikus et al. |
| 2002/0183827 A1 | 12/2002 | Derus et al. |
| 2003/0050686 A1 | 3/2003 | Raeder-Devens et al. |
| 2003/0167060 A1 | 9/2003 | Buzzard et al. |
| 2004/0019359 A1 | 1/2004 | Worley et al. |
| 2004/0193180 A1 | 9/2004 | Buzzard et al. |
| 2004/0193243 A1 | 9/2004 | Mangiardi et al. |
| 2004/0267281 A1 | 12/2004 | Harari et al. |
| 2005/0090887 A1 | 4/2005 | Pryor |
| 2005/0125050 A1 | 6/2005 | Carter et al. |
| 2005/0149160 A1 | 7/2005 | McFerran et al. |
| 2005/0209653 A1 | 9/2005 | Herbert et al. |
| 2005/0267555 A1 | 12/2005 | Marnfeldt et al. |
| 2005/0278010 A1 | 12/2005 | Richardson et al. |
| 2006/0200222 A1 | 9/2006 | Johnson et al. |
| 2007/0043421 A1 | 2/2007 | Mangiardi et al. |
| 2007/0088418 A1 | 4/2007 | Jacobson |
| 2007/0100421 A1 | 5/2007 | Griffin |
| 2007/0191864 A1 | 8/2007 | Shumer |
| 2007/0208350 A1 | 9/2007 | Gunderson |
| 2007/0270932 A1 | 11/2007 | Headley et al. |
| 2008/0021532 A1 | 1/2008 | Kveen et al. |
| 2009/0099636 A1 | 4/2009 | Chanduszko et al. |
| 2009/0118740 A1 | 5/2009 | Mangiardi et al. |
| 2009/0192518 A1 | 7/2009 | Golden et al. |
| 2009/0281605 A1 | 11/2009 | Marnfeldt et al. |
| 2010/0004732 A1 | 1/2010 | Johnson et al. |
| 2010/0049295 A1 | 2/2010 | Satasiya et al. |
| 2010/0274227 A1 | 10/2010 | Khairkhahan et al. |
| 2011/0009944 A1 | 1/2011 | Moser |
| 2011/0034939 A1 | 2/2011 | Kveen et al. |
| 2011/0112548 A1 | 5/2011 | Fifer et al. |
| 2011/0237967 A1 | 9/2011 | Moore et al. |
| 2011/0238077 A1 | 9/2011 | Wenger |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0095539 A1 | 4/2012 | Khairkhahan et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0116741 A1 | 5/2013 | Bornzin et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold |
| 2014/0018818 A1 | 1/2014 | Somogyi et al. |
| 2014/0031836 A1 | 1/2014 | Ollivier |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |
| 2014/0249543 A1 | 9/2014 | Berthiaume et al. |
| 2014/0257324 A1 | 9/2014 | Fain |
| 2014/0303704 A1 | 10/2014 | Suwito et al. |
| 2014/0378991 A1 | 12/2014 | Ollivier |
| 2015/0045868 A1 | 2/2015 | Bonner et al. |
| 2015/0051615 A1 | 2/2015 | Schmidt et al. |
| 2015/0094668 A1 | 4/2015 | Wood et al. |
| 2015/0094735 A1 | 4/2015 | Ward et al. |
| 2015/0112361 A1 | 4/2015 | Khairkhahan et al. |
| 2015/0148815 A1 | 5/2015 | Steingisser et al. |
| 2015/0273207 A1* | 10/2015 | Tran ............... A61N 1/059 607/126 |
| 2015/0273212 A1 | 10/2015 | Berthiaume et al. |
| 2015/0283376 A1 | 10/2015 | Ollivier |
| 2015/0335884 A1 | 11/2015 | Khairkhahan et al. |
| 2015/0352351 A1 | 12/2015 | Muessig et al. |

(56) References Cited

U.S. PATENT DOCUMENTS

| | | |
|---|---|---|
| 2016/0000563 A1 | 1/2016 | Asleson et al. |
| 2016/0015287 A1 | 1/2016 | Anderson et al. |
| 2016/0015322 A1 | 1/2016 | Anderson et al. |
| 2016/0015968 A1 | 1/2016 | Bonner et al. |
| 2016/0015983 A1 | 1/2016 | Sheldon et al. |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0096001 A1 | 4/2016 | Eidenschink et al. |
| 2016/0114157 A1 | 4/2016 | Haasl et al. |
| 2016/0129239 A1 | 5/2016 | Anderson |
| 2016/0143661 A1 | 5/2016 | Wood et al. |
| 2016/0206872 A1 | 7/2016 | Wood et al. |
| 2016/0209653 A1 | 7/2016 | Choi |
| 2016/0213919 A1 | 7/2016 | Suwito et al. |
| 2016/0220829 A1 | 8/2016 | Wood |
| 2016/0235971 A1 | 8/2016 | Wood et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0310703 A1 | 10/2016 | Drake et al. |
| 2016/0310747 A1 | 10/2016 | Grubac et al. |
| 2016/0325104 A1 | 11/2016 | Anderson et al. |

FOREIGN PATENT DOCUMENTS

| | | |
|---|---|---|
| EP | 0274846 A1 | 7/1988 |
| EP | 0361314 A2 | 4/1990 |
| EP | 0364420 A1 | 4/1990 |
| EP | 0732087 A1 | 9/1996 |
| EP | 0872220 A1 | 10/1998 |
| WO | 9315790 A1 | 8/1993 |
| WO | 9631174 A1 | 10/1996 |
| WO | 0078246 A2 | 12/2000 |
| WO | 02087470 A1 | 11/2002 |
| WO | 03090644 A1 | 11/2003 |
| WO | 2004030571 A2 | 4/2004 |
| WO | 2005070095 A2 | 8/2005 |
| WO | 2008042266 A2 | 4/2008 |
| WO | 2013066883 A1 | 5/2013 |

\* cited by examiner

DELIVERY DEVICES AND METHODS FOR LEADLESS CARDIAC DEVICES

CROSS-REFERENCE TO RELATED APPLICATIONS

This application claims the benefit of U.S. Provisional Patent Application Ser. No. 62/258,064 filed on Nov. 20, 2015, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, a delivery system for delivering an implantable leadless pacing device may comprise a tubular member including a lumen extending from a proximal end to a distal end thereof, the tubular member including a distal holding section defining a cavity therein, a handle assembly, and an implantable leadless pacing device configured to be disposed within the cavity of the distal holding section. The leadless pacing device may comprise a housing having a proximal end and a distal end, a fixation mechanism disposed adjacent the distal end, and a tether retention feature disposed adjacent to the proximal end. The delivery system may further comprise a tether configured to releasably secure the implantable leadless pacing device to the delivery device, the tether may be releasably coupled to the tether retention feature of the leadless pacing device and extending to the handle assembly of the delivery device.

Alternatively or additionally to any of the examples above, in another example, the tether may have a tensile strength in the range of 26.7 Newtons (N) to 89.0 N.

Alternatively or additionally to any of the examples above, in another example, the tether may have a tensile strength in the range of 35.6 N to 44.5 N.

Alternatively or additionally to any of the examples above, in another example, the tether may have a modulus of elasticity in the range of 96.5 gigapascals (GPa) to 131 GPa.

Alternatively or additionally to any of the examples above, in another example, the tether may have a coefficient of friction of less than 0.05.

Alternatively or additionally to any of the examples above, in another example, the tether may comprise a monofilament ultra-high-molecular-weight polyethylene (UHMWPE).

Alternatively or additionally to any of the examples above, in another example, the tether may comprise a multifilament UHMWPE.

Alternatively or additionally to any of the examples above, in another example, the tether may comprise a monofilament polyether ether ketone (PEEK).

Alternatively or additionally to any of the examples above, in another example, the tether may comprise a polytetrafluoroethylene (PTFE) coated nitinol wire or cable.

Alternatively or additionally to any of the examples above, in another example, the tether may comprise an ethylene tetrafluoroethylene (ETFE) coated nitinol wire or cable.

Alternatively or additionally to any of the examples above, in another example, the tether retention feature may be incorporated with a docking member of the leadless pacing device.

Alternatively or additionally to any of the examples above, in another example, the tether may be configured to pass through an opening in the tether retention feature.

Alternatively or additionally to any of the examples above, in another example, the tether may form a loop.

Alternatively or additionally to any of the examples above, in another example, a proximal end of the tether may be configured to be actuated to perform a fixation test on the leadless pacing device.

Alternatively or additionally to any of the examples above, in another example, a proximal end of the tether may be secured to a cap in the handle assembly.

In another example, a delivery system for delivering an implantable leadless pacing device may comprise a delivery device. The delivery device may comprise a tubular member including a lumen extending from a proximal end to a distal end thereof, the tubular member including a distal holding section defining a cavity therein and a handle assembly. The delivery system may further comprise an implantable leadless pacing device configured to be disposed within the cavity of the distal holding section. The leadless pacing device may comprise a housing having a proximal end and a distal end, a fixation mechanism disposed adjacent the distal end, and a tether retention feature disposed adjacent to the proximal end. The delivery system may further comprise a tether configured to releasably secure the implantable leadless pacing device to the delivery device, the tether may be releasably coupled to the tether retention feature of the leadless pacing device and extending to the handle assembly of the delivery device.

Alternatively or additionally to any of the examples above, in another example, the tether may have a tensile strength in the range of 26.7 Newtons (N) to 89.0 N.

Alternatively or additionally to any of the examples above, in another example, the tether may have a tensile strength in the range of 35.6 N to 44.5 N.

Alternatively or additionally to any of the examples above, in another example, the tether may have a modulus of elasticity in the range of 96.5 gigapascals (GPa) to 131 GPa.

Alternatively or additionally to any of the examples above, in another example, the tether may have a coefficient of friction of less than 0.05.

Alternatively or additionally to any of the examples above, in another example, the tether may comprise a monofilament ultra-high-molecular-weight polyethylene (UHMWPE).

Alternatively or additionally to any of the examples above, in another example, the tether may comprise a multifilament UHMWPE.

Alternatively or additionally to any of the examples above, in another example, the tether may comprise a monofilament polyether ether ketone (PEEK).

Alternatively or additionally to any of the examples above, in another example, the tether may comprise a polytetrafluoroethylene (PTFE) coated nitinol wire or cable.

Alternatively or additionally to any of the examples above, in another example, the tether may comprises an ethylene tetrafluoroethylene (ETFE) coated nitinol wire or cable.

In another example, a delivery system for delivering an implantable leadless pacing device may comprise a delivery device. The delivery device may comprise a tubular member including a lumen extending from a proximal end to a distal end thereof, the tubular member including a distal holding defining a cavity therein and a handle assembly. The delivery system may further comprise an implantable leadless pacing device configured to be disposed within the cavity of the distal holding section. The leadless pacing device may comprise a housing having a proximal end and a distal end, a fixation mechanism disposed adjacent the distal end, and a docking member comprising a tether retention loop disposed adjacent to the proximal end. The delivery system may further comprise a tether comprising a length of material having a first end and a second end and may be configured to releasably secure the implantable leadless pacing device to the delivery device, the tether looped around the tether retention loop and extending to the handle assembly of the delivery device.

Alternatively or additionally to any of the examples above, in another example, the tether may have a tensile strength in the range of 35.6 Newtons (N) to 44.5 N.

Alternatively or additionally to any of the examples above, in another example, the tether may have a modulus of elasticity in the range of 96.5 gigapascals (GPa) to 131 GPa.

Alternatively or additionally to any of the examples above, in another example, the tether may have a coefficient of friction of less than 0.05.

Alternatively or additionally to any of the examples above, in another example, the tether may comprise a monofilament ultra-high-molecular-weight polyethylene (UHMWPE).

Alternatively or additionally to any of the examples above, in another example, the tether may comprise a multifilament UHMWPE.

Alternatively or additionally to any of the examples above, in another example, the tether may comprise a monofilament polyether ether ketone (PEEK).

Alternatively or additionally to any of the examples above, in another example, the tether may comprise a polytetrafluoroethylene (PTFE) coated nitinol wire or cable.

Alternatively or additionally to any of the examples above, in another example, the tether may comprise an ethylene tetrafluoroethylene (ETFE) coated nitinol wire or cable.

In another example, a delivery system for delivering an implantable leadless pacing device may comprise a delivery device. The delivery device may comprise a tubular member including a lumen extending from a proximal end to a distal end thereof, the tubular member including a distal holding section defining a cavity therein, a pusher member extending through the lumen of the tubular member, and a handle assembly configured to actuate the pusher member relative to the tubular member. The delivery system may further comprise an implantable leadless pacing device configured to be disposed within the cavity of the distal holding section. The leadless pacing device may comprise a housing having a proximal end and a distal end, a fixation mechanism disposed adjacent the distal end, and a docking member comprising a tether retention loop disposed adjacent to the proximal end. The delivery system may further comprise a tether comprising a length of material having a first end and a second end and may be configured to releasably secure the implantable leadless pacing device to the delivery device, the tether looped around the tether retention loop and extending to the handle assembly of the delivery device. The tether may have a tensile strength in the range of 35.6 Newtons (N) to 44.5 N, a modulus of elasticity in the range of 96.5 gigapascals (GPa) to 131 GPa, and a coefficient of friction of less than 0.05.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

DETAILED DESCRIPTION

Figure 1:
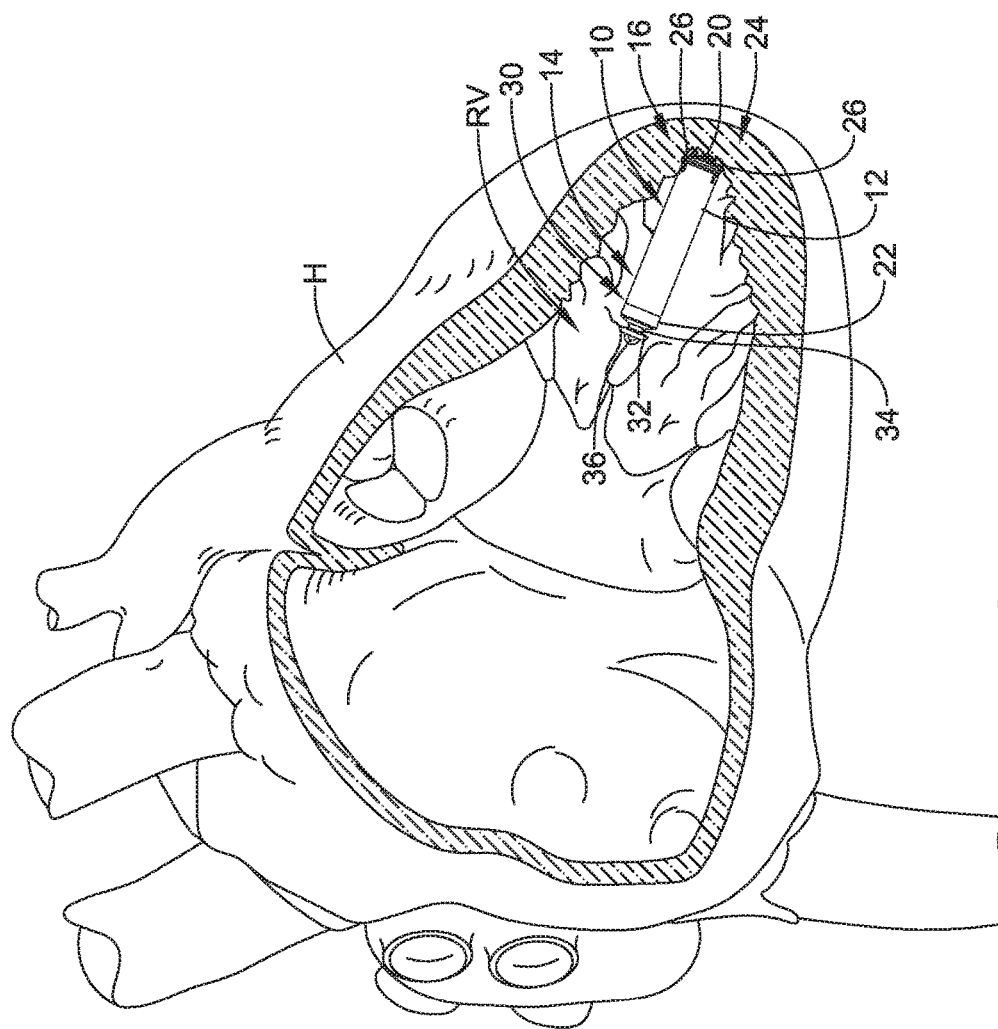
FIG. 1 is a plan view of an example leadless pacing device implanted within a heart.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. The capsule may be delivery to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature.

Figure 2:
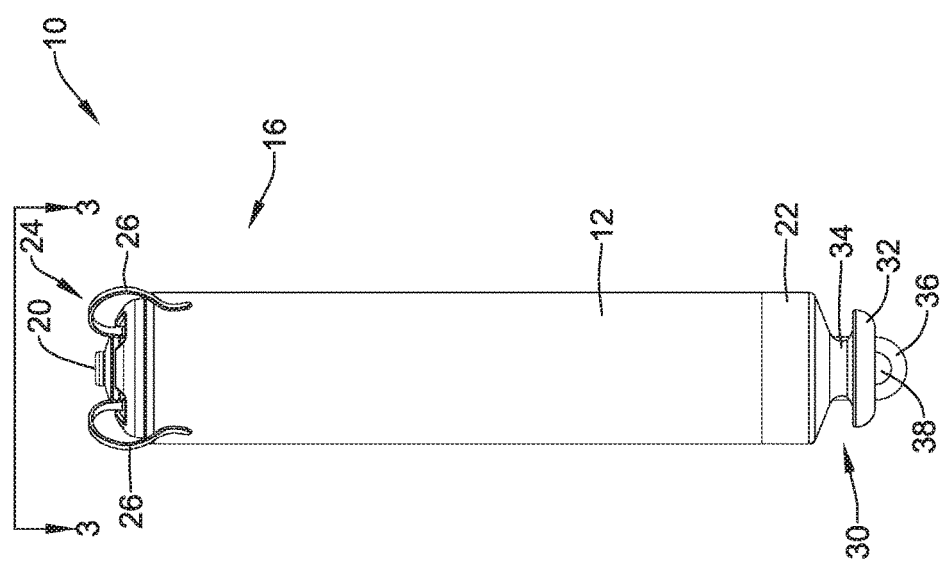
FIG. 2 is a side view of an example implantable leadless cardiac pacing device.
Figure 3:
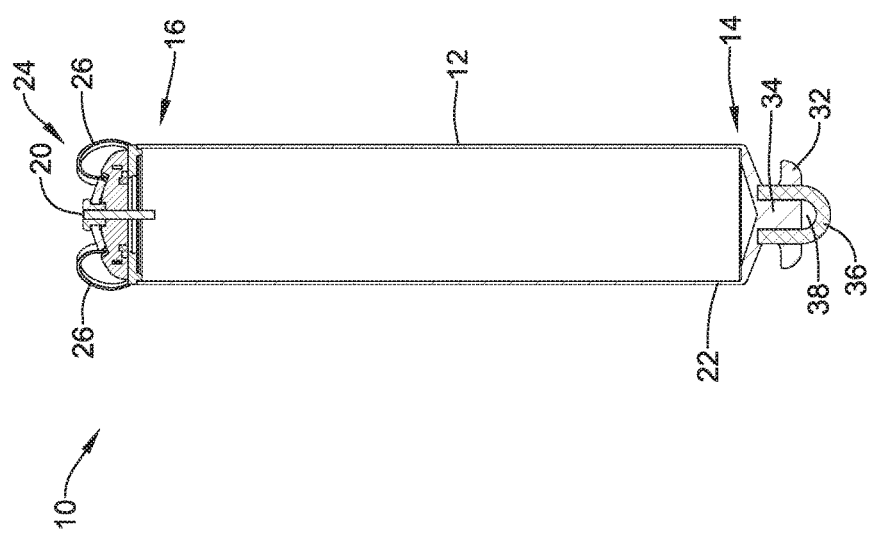
FIG. 3 is a cross-sectional view of the implantable leadless cardiac pacing device of FIG. 2.

FIG. 1 illustrates an example implantable leadless cardiac pacing device 10 (e.g., a leadless pacemaker) implanted in a chamber of a heart H, such as the right ventricle RV. A side view of the illustrative implantable device 10 is shown in FIG. 2 and a cross-sectional view of the illustrative implantable device 10, taken at line 3-3 in FIG. 2, is illustrated in FIG. 3. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks or tines 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The retention structure 36 may extend though the head portion 32, along the neck portion 34, and to or into the proximal end 14 of the housing 12, as is shown more clearly in FIG. 3. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 4:
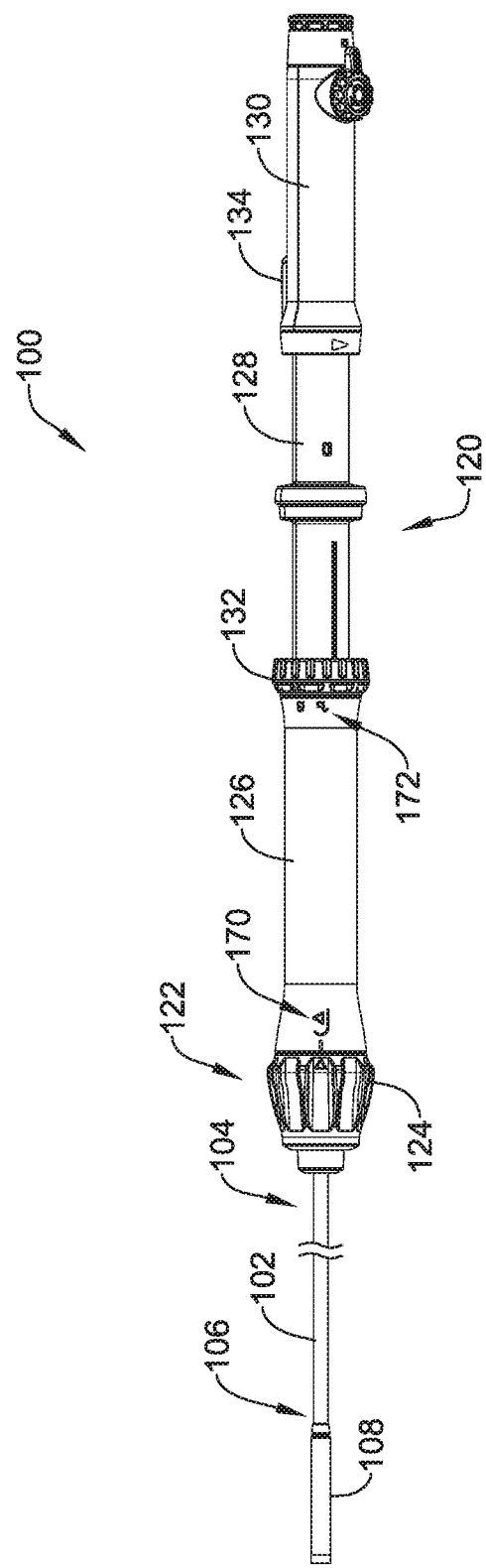
FIG. 4 is a plan view of an example delivery device for an implantable leadless cardiac pacing device.

FIG. 4 is a plan view of an illustrative delivery device 100, such as a catheter, that may be used to deliver the implantable device 10. The delivery device 100 may include an outer tubular member 102 having a proximal section 104 and a distal section 106. An intermediate tubular member 110 may be longitudinally slidably disposed within a lumen 150 of the outer tubular member 102 (see e.g. FIG. 5). An inner tubular member 116 may be longitudinally slidably disposed within a lumen 152 of the intermediate tubular member 110 (see e.g. FIG. 5). A distal holding section 108 may be attached to a distal end portion 114 of the intermediate tubular member 110. The delivery device 100 may also include a handle assembly 120 positioned adjacent to the proximal section 104 of the outer tubular member 102. In some embodiments, the outer tubular member 102 may include at least a section thereof that has an outer diameter D2 that is less than the outer diameter D1 of at least a portion of the holding section 108 (see e.g. FIG. 5).

Figure 5:
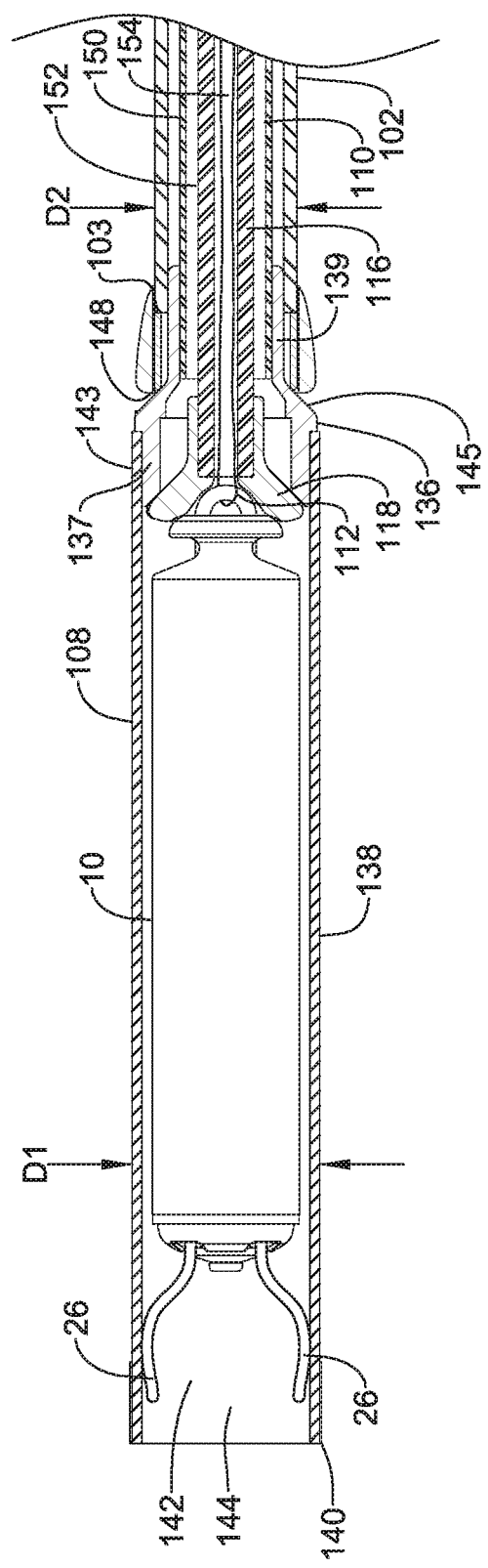
FIG. 5 is a partial cross-sectional side view of the distal portion of the delivery device of FIG. 4.

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g. FIG. 5). The first hub portion 126, second hub portion 128, and third hub portion 130 may be positioned in a generally telescoping arrangement and longitudinally slidable relative to each other. As will be discussed in more detail below, each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously. The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116, as will be discussed in more detail below. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the intermediate tubular member 110, as will be discussed in more detail below.

The distal holding section 108 may be configured to receive the implantable device 10 therein. For example, referring to FIG. 5, which illustrates a cross-sectional view of a distal portion of delivery device 100, the holding section 108 may define a cavity 142 for slidably receiving the implantable device 10, and may include a distal opening 144 for slidable insertion and/or extraction of the implantable device 10 into and/or out of the cavity 142.

The distal holding section 108 may include a body portion 138 and a distal tip portion 140 that may be, for example, configured to be atraumatic to anatomy, such as a bumper tip. For example, as the catheter is navigated through the anatomy, the distal tip may come into contact with anatomy. Additionally, when the catheter is used to deliver the device, the tip 140 of the delivery device 100 will likely come into contact with tissue adjacent the target site (e.g. cardiac tissue of the heart). A hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma.

For example, the distal tip 140 may be made of a material that is softer than the body portion 138 of the distal holding section. In some cases, the distal tip 140 may include a material that has a durometer that is less than the durometer of the material of the body portion 138. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is that is rounded or includes a curvature configured to be more atraumatic to tissue.

In some embodiments, all or a portion of the distal holding section 108 may include an inner surface that may be configured to resist getting caught on the fixation mechanism 24, such as the one or more, or a plurality of hooks or tines 26 on the device 10. For example, the distal holding section 108 may include an inner layer or coating of harder or more lubricious material that resists force applied by the fixation mechanism 24 onto the inner surface of the distal holding section 108. For example, the distal holding section 108 may include a multi-layered structure, and an inner layer may be made of a material that is harder than an outer layer.

The inner tubular member 116 may be disposed (e.g., slidably disposed) within a lumen 152 of the intermediate tubular member 110. The inner tubular member 116 may be engaged by a user near or at the third hub portion 130, and extend through a lumen 152 of the intermediate tubular member 110 and into the distal holding section 108. A distal portion 118 of the inner tubular member 116 may be capable of engaging the device 10, and the inner tubular member 116 may be used to "push" the device 10 out from distal holding section 108 so as to deploy and anchor device 10 within a target region (e.g., a region of the heart such as the right ventricle). The inner tubular member 116 may have a lumen 154 extending from the proximal end 117 to a distal portion 118 thereof.

During delivery of the device 10, a clinician may wish to test the securement of the device 10 to the tissue and verify its electrical performance prior to permanently releasing the device 10. To enable evaluation of these parameters, a tether 112 may be used to releasably secure the device 10 to the delivery device 100. The tether 112 may maintain a connection to the device 10 while also enabling excess tether 112 to extend distally beyond the distal end of the delivery device 100 (see FIG. 10E). This may allow the device 10 to be decoupled from the delivery device 100 for the evaluation of the electrical performance (thus minimizing any influence from the delivery device on the electrode) while still maintaining a connection between the device 10 and the delivery device 100. The tether 112 may also be used to evaluate the fixation of the device 10. A "tug test" may be performed by tugging or pulling on the proximal end of the tether 112 to visually confirm securement of the device 10. Once acceptable performance has been identified, the tether 112 may be released or uncoupled from the device 10. In some instances, the tether 112 may be a single or unitary length of material that may extend from a proximal end 117 of the lumen 154, out through the distal portion 118, through the opening 38 of the device 10 and return to the proximal end 117 of the inner tubular member 116 such that both ends of the tether 112 are positioned adjacent to the third hub portion 130. In some instances, as will be discussed in more detail below, the ends of the tether 112 may be secured within a locking feature in the third hub portion 130. In other embodiments, the tether 112 may be a single length of material with loose ends secured together to form a loop. In yet other embodiments, the tether 112 may be formed as a single continuous loop with no joining features.

It is contemplated that the tether 112 may be made of a material which allows for a lubricious, strong, no stretch, no memory tether. Current implantable suture materials may not be ideal for this application for several reasons. Multifilament suture material (e.g. polyester, silk) provide good strength, minimal stretch, and no memory, however, it does not slide well across itself, especially if twisted. This may cause removal of the tether 112 to be difficult to remove if it becomes twisted or tangled. Monofilament suture material (e.g. polypropylene, nylon) provides good strength and lubricity, but stretches significantly. This may make it difficult to perform a fixation evaluation or tug test.

The tether 112 may have a cross-sectional dimension in the range of 0.001 inches to 0.015 inches (0.0254 millimeters to 0.381 millimeters). The tether 112 should be made from a material that is lubricious enough that it easily slides against itself and the tether retention device 36 of the device 10. This may allow for easy removal of the tether 112 as well as minimize tangling of tether 112 strands within the delivery device 100. In some instances, the tether 112 may be formed from a material having a coefficient of friction of less than 0.05. The tether 112 may also be formed of a material having a tensile strength in the range of 6 to 20 pounds (lbf) (26.7 Newtons N to 89.0 N). In some instances, the material may have a minimum tensile strength of about 8 lbf (35.6 N) or about 10 lbf (44.5 N). It is further contemplated that the tether 112 may be formed from a material that has a modulus of elasticity in the range of 14.0 and 19.0 megapounds per square inch (Mpsi) (96.5-131 gigapascals (GPa)) such that the tether 112 has minimal or no stretching under an applied force (for example, during the tug test). Some materials having the above noted properties may include, but are not limited to monofilament ultra-high-molecular-weight polyethylene (UHMWPE), multifilament UHMWPE, monofilament polyether ether ketone (PEEK), multifilament PEEK, polytetrafluoroethylene (PTFE) coated nitinol wire or cable, ethylene tetrafluoroethylene (ETFE) coated nitinol wire or cable, and/or other materials that exhibit similar properties.

In order to more specifically place or steer the delivery device 100 to a position adjacent to the intended target, the delivery device 100 may be configured to be deflectable or articulable or steerable. Referring to FIG. 4, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the holding section 108 is in a desirable position or orientation for navigation or delivery of the device 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a desired mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the outer tubular member 102 to be predisposed to be bent and/or deflected in a certain direction or configuration when compression and/or tension forces are applied thereto. It is contemplated that the outer tubular member 102 may be a laser cut metallic tubing, a braid reinforced polymeric tubing, or other flexible tubular structure as desired.

Returning again to FIG. 5, the distal holding section 108 may be affixed to a distal end portion 114 of the intermediate tubular member 110. The distal holding section 108 may include a hub portion 136 and a tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some embodiments, the outer tubular member 102 may include a metal ring or tip adjacent the distal end 103 thereof for attaching one or more pull wires thereto. It is contemplated that the outer tubular member 102 may further include a lubricious liner, such as, but not limited to, a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. It is contemplated that the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surface may engage as the proximal end portion 139 is proximally retracted within the outer tubular member 102. Other coupling arrangements may be used as desired.

It is contemplated that as the outer tubular member 102 is bent to navigate the implantable device 10 to the desired location, the proximal end portion 139 may advance distally and disengage from the inner surface of the outer tubular member 102 creating a kink point or weakened region adjacent to the bonding region 146. Proximally retracting the intermediate tubular member 110 to bring the intermediate region 145 into contact with the outer tubular member 102 at contact point 148 and/or bringing the proximal end portion 139 into the outer tubular member 102 and fixing the intermediate tubular member 110 in this configuration may help prevent migration of the distal holding section 108 during navigation of the delivery device 100 to the desired location. Such a configuration may also place the intermediate tubular member 110 in tension while the distal holding section 108 applies a compression force on the outer tubular member 102, as will be discussed in more detail below. As discussed above, a locking mechanism 132 in the handle assembly 120 may be utilized to releasably maintain the outer tubular member 102 and the intermediate tubular member 110 in a desired orientation.

Figure 6:
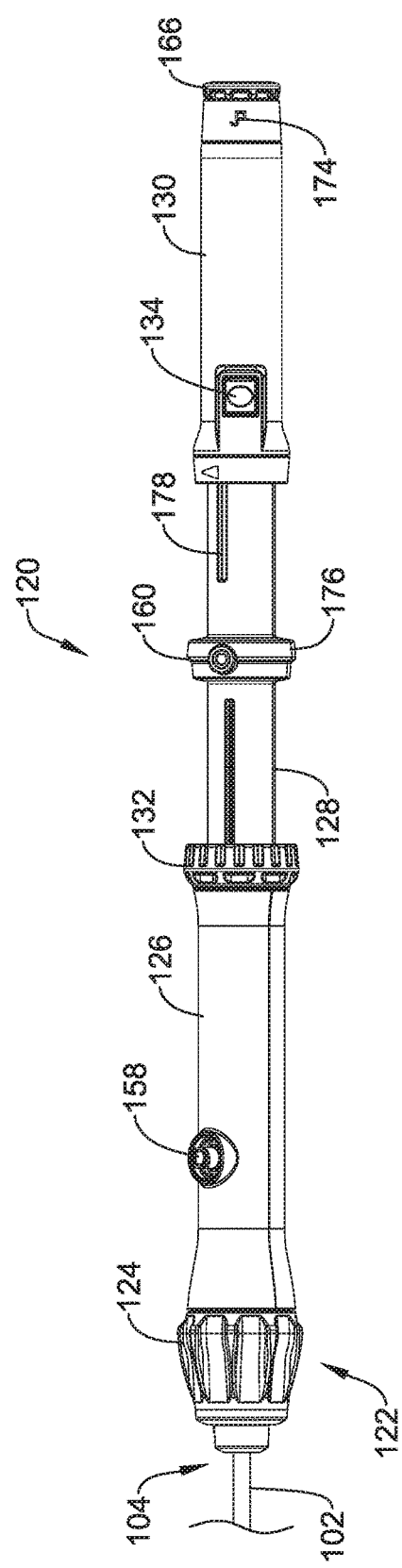
FIG. 6 is a top view of the handle of the illustrative delivery device of FIG. 4.
Figure 7:
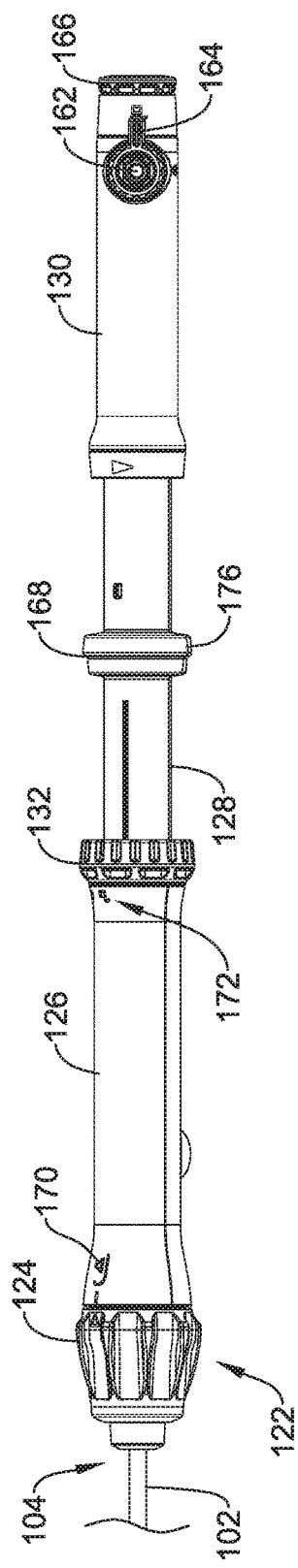
FIG. 7 is a bottom view of the handle of the illustrative delivery device of FIG. 4.

FIG. 6 illustrates a top view of the handle assembly 120 of the delivery device 100. FIG. 7 illustrates a bottom view of the handle assembly, approximately 180° from the view shown in FIG. 6. The handle assembly 120 may include one or more ports 158, 160, 162 for delivering fluids, such as, but not limited to, a contrast and/or flushing fluid to the cavity 142 of the distal holding section 108. The flush ports 158, 160, 162 may be in fluid communication with the lumens 150, 152, 154 of the outer, intermediate or inner tubular members 102, 110, 116, as desired. For example, the flush port 158 may be in fluid communication with the lumen 150 of the outer tubular member 102, the flush port 160 may be in fluid communication with the lumen 152 of the intermediate tubular member 110, and the flush port 162 may be in fluid communication with the lumen 154 of the inner tubular member 116.

The handle assembly 120 may further include a tether lock 164. The tether lock 164 may be actuatable between a locked and an unlocked configuration to maintain the tether 112 in a desired orientation. The ends of the tether 112 may affixed to, secured to, or otherwise engage a tether cap 166 positioned at a proximal end of the third hub portion 130. The tether cap 166 may be removably secured to the third hub portion 130 to allow a clinician access to the ends of the tether 112. When the tether lock 164 is in the locked configuration, the tether cap 166 may not be removed from the third hub portion 130. When the tether lock 164 is in the unlocked configuration, the tether cap 166 may be removed and the ends of the tether 112 may be actuated. For example, once the device 10 has been implanted and its location verified, the tether 112 may be removed from the tether retention feature 36 of the device 10 by pulling on one of the ends until the opposite end has passed through the opening 38 such that the device 10 is free from the tether 112.

In some instances, the handle assembly 120 may also include visual markings, such as, but not limited to the markings illustrated at 170, 172, 174. These markings 170, 172, 174 may provide visual instructions or indications to the clinician. For example, the marking shown at 170 may be positioned proximate the rotatable member 124 of the actuation mechanism 122 to indicate that the rotatable member 124 controls deflection of the outer tubular member 102 and/or to indicate which direction the distal end region 106 will deflect when the rotatable member 124 of the actuation mechanism 122 is rotated in a given direction. The markings shown at 172 may provide an indication of whether the second locking mechanism 132 is in the unlocked and/or locked configuration. Similarly, the markings shown at 174 may provide an indication of whether the tether lock 164 is in the unlocked and/or locked configuration.

Figure 8:
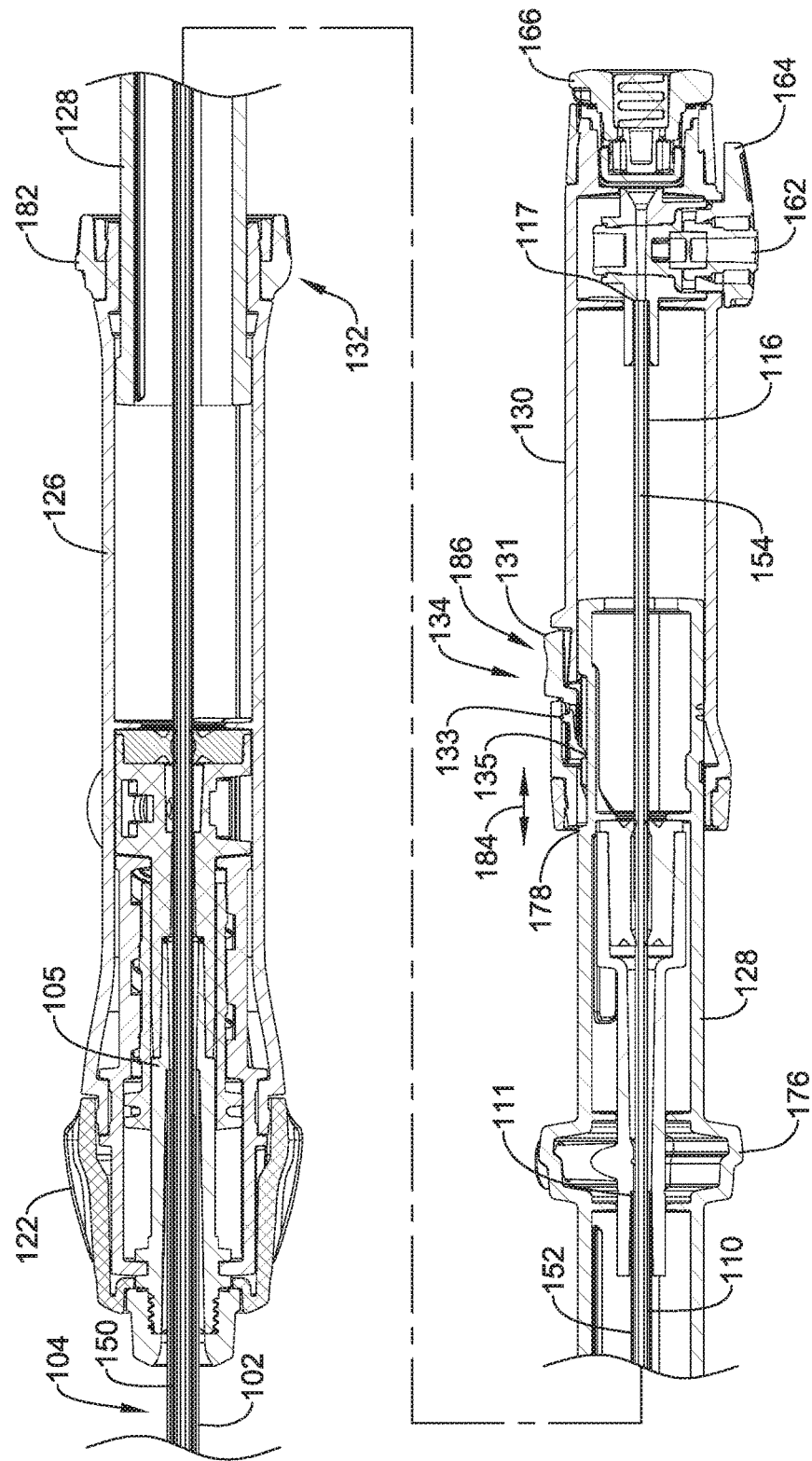
FIG. 8 is a cross-section view of the handle of the illustrative delivery device of FIG. 4 taken at line 8-8 in FIG. 6.

FIG. 8 illustrates a cross-sectional view of the handle assembly 120 of the delivery device. As discussed above, the handle assembly 120 may include a first hub portion 126 attached to the proximal end section 104 of the outer tubular member 102, a second hub portion 128 attached to a proximal end section of the intermediate tubular member 110, and a third hub portion 130 attached to a proximal end section of the inner tubular member 116. Each of the first hub portion 126, the second hub portion 128, and the third hub portion 130 may be slidable and rotatable relative to each other such that the outer tubular member 102, intermediate tubular member 110, and inner tubular member 116 may be individually longitudinally actuated.

The inner tubular member 116 may extend distally from a proximal end 117. The proximal end 117 of the inner tubular member 116 may be positioned within or adjacent to the tether lock 164. The tether lock 164 may include a port 162 which may be in fluid communication with a lumen 154 of the inner tubular member 116. The lumen 154 may extend from the proximal end 117 to the distal portion 118 for delivering fluids, such as, but not limited to, a contrast and/or flushing fluid to the cavity 142 of the distal holding section 108. In some instances, the inner tubular member 116 may be coupled or affixed to the third hub portion 130 adjacent the proximal end 117 of the inner tubular member 116, although this is not required. It is contemplated that the inner tubular member 116 may be affixed to the third hub portion 130 at any longitudinal location desired. In some instances, a tether, such as tether 112, for securing the implantable device 10 to the distal portion 118 of the inner tubular member 116 may be disposed within the lumen 154 and may exit the delivery device 100 through or adjacent to tether cap 166, although this is not required.

The intermediate tubular member 110 may extend distally from a proximal end 111. The proximal end 111 of the intermediate tubular member 110 may be positioned within the second hub portion 128. The intermediate tubular member 110 may include a lumen 152 extending from the proximal end 111 to a distal end of the intermediate tubular member 110. The inner tubular member 116 may be slidably disposed within the lumen 152 of the intermediate tubular member 110. In some instances, the intermediate tubular member 110 may be coupled or affixed to the second hub portion 128 adjacent the proximal end 111 of the intermediate tubular member 110, although this is not required. It is contemplated that the intermediate tubular member 110 may be affixed to the second hub portion 128 at any longitudinal location desired.

The outer tubular member 102 may extend distally from a proximal end 105. The proximal end 105 of the outer tubular member 102 may be positioned within the first hub portion 126. The outer tubular member 102 may include a lumen 150 extending from the proximal end 105 to a distal end 103 of the outer tubular member 102. The intermediate tubular member 110 may be longitudinally slidably disposed within the lumen 150 of the outer tubular member 102. In some instances, the outer tubular member 102 may be coupled or affixed to the first hub portion 126 adjacent the proximal end 105 of the outer tubular member 102, although this is not required. It is contemplated that the outer tubular member 102 may be affixed to the first hub portion 126 at any longitudinal location desired.

In some instances, the first hub portion 126 may include a retaining ring 182 positioned adjacent to a proximal end of the first hub portion 126. In some instances, the retaining ring 182 may be rotatable about a longitudinal axis of the handle assembly 120. It is further contemplated that the retaining ring 182 may include locking features configured to engage with other locking features of the locking mechanism 132. When the retaining ring 182 engages other features of the locking mechanism 132, longitudinal movement of the first hub portion 126 and the second hub portion 128 relative to one another may be prevented. Rotating the retaining ring 182 may disengage the retaining ring 182 from the other features of the locking mechanism 132. This may allow for longitudinal movement of the first hub portion 126 and the second hub portion 128 relative to one another, as will be described in more detail below. While the second locking mechanism 132 is described as a rotating retaining ring 182, it is contemplated that other locking mechanisms capable of releasably securing first hub portion 126 and the second hub portion 128, and thus the outer tubular member 102 and the intermediate tubular member 110, are contemplated.

In some instances, the first locking mechanism 134 may include a depressible button 131. The depressible button 131 may include a first outwardly protruding portion 133 configured to engage a region of the third hub portion 130 and a second inwardly protruding portion 135 configured to engage a region of the second hub portion 128. For example, the second protruding portion 135 may be disposed in and engage a groove or recess 178 formed in the second hub portion 128. The engagement of the first locking mechanism 134 may prevent or reduce relative movement of the second hub portion 128 and the third hub portion 130 when the first locking mechanism 134 is not actively actuated (e.g. depressed) by a clinician. A downward force 186 may be applied to the button 131. The force 186 may cause the first protruding portion 133 to lower and/or disengage from a surface of the third hub portion 130 and the second protruding portion 135 to raise and/or disengage from a surface of the second hub portion 128. This may allow the third hub portion 130 to be moved longitudinally (e.g., proximally and/or distally), as shown at 184, along a longitudinal axis of the handle assembly 120 relative to the second hub portion 128, as will be discussed in more detail below. Longitudinal actuation of the third hub portion 130 relative to the second hub portion 128 may result in a corresponding longitudinal actuation of the inner tubular member (and hence device 10) relative to intermediate tubular member 110 and distal holding section 108. Such actuation may be used to incrementally deploy the device 10. FIG. 8 illustrates the second protruding portion 135 disposed in the middle of the recess 178. However, it is contemplated that during advancement of the delivery device 100 to the desired treatment location, the second protruding portion 135 may be positioned at the proximal end of the recess 178 to ensure the device 10 is fully disposed in the distal holding section 108. This is just an example. While the first locking mechanism 134 is described as a depressible button 131, it is contemplated that other locking mechanisms capable of releasably securing the second hub portion 128 and the third hub portion 130, and thus the intermediate tubular member 110 and the inner tubular member 116, are contemplated.

Figure 9:
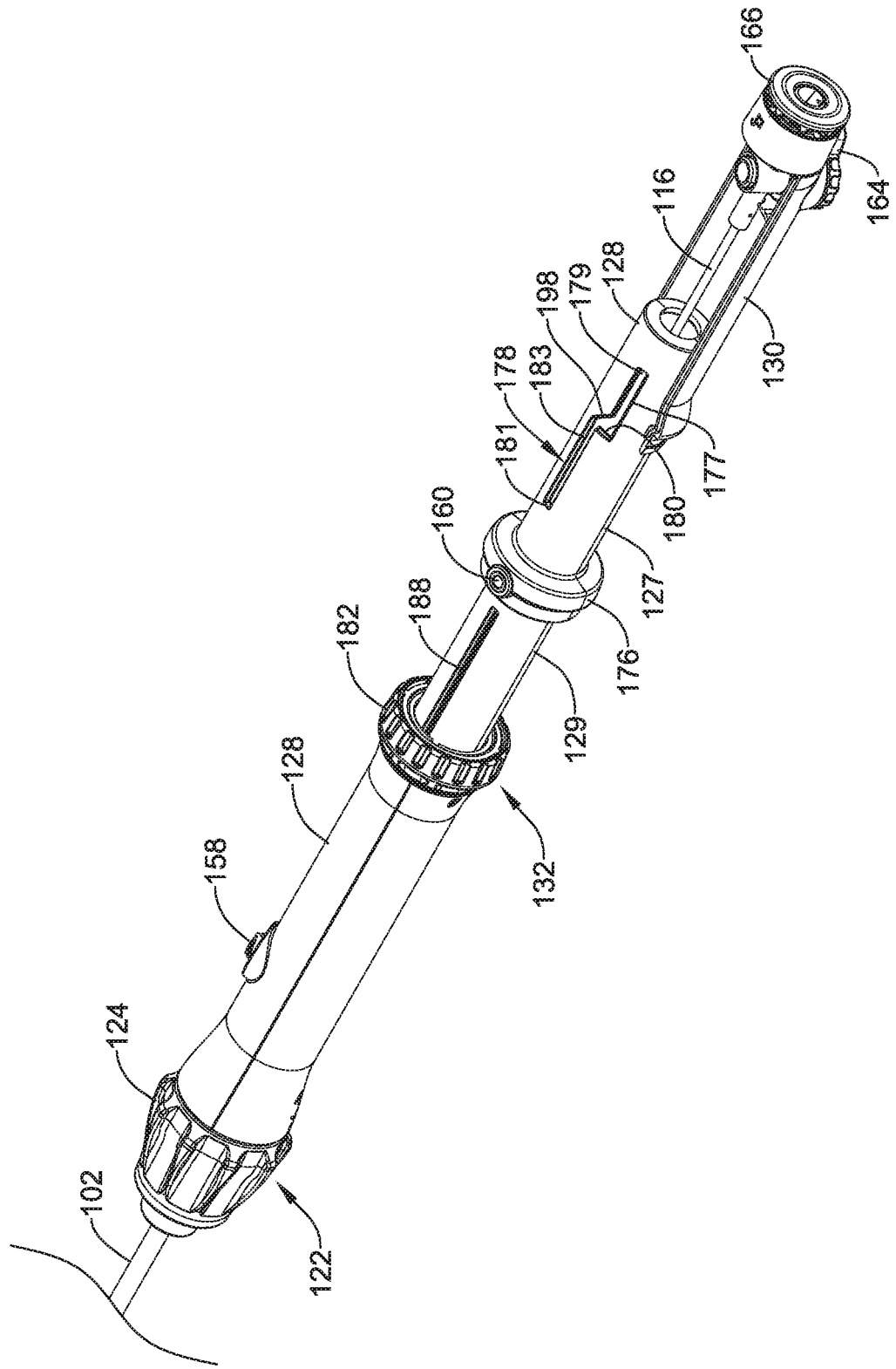
FIG. 9 is a perspective view of the handle of the illustrative delivery device of FIG. 4 with portions removed.

FIG. 9 illustrates a partial perspective view of the handle assembly 120 with portions of the third hub portion 130 removed to more clearly illustrate features of the second hub portion 128. A proximal portion 127 of the second hub portion 128 may include a groove or recess 178 formed therein. The groove 178 may extend from a proximal end 179 to a distal end 181. In some embodiments, groove 178 may include a proximal portion 177 and a distal portion 183 which may be circumferentially offset from one another. A hard stop 180 may be provided at a region between the proximal end 179 and the distal end 181. The hard stop 180 may be a wall or other protrusion configured to engage the second protruding portion 135 of the first locking mechanism 134 such that in order to advance the second protruding portion 135 distally past the hard stop 180 from the proximal portion 177, the user must rotate the third hub portion 130 to align the second protruding portion 135 with the distal portion 183 of the groove 178. This may allow the device 10 to be incrementally deployed. During advancement of the delivery device 100 through the vasculature, the second protruding portion 135 may be disposed within the proximal portion 177 adjacent to the proximal end 179. As discussed above, the second protruding portion 135 may engage a surface of the second hub portion 128 to prevent and/or minimize relative movement of the second and third hub portions 128, 130 relative to one another.

The groove 178 may also include an angled region 198 between the proximal portion 177 and the distal portion 183 positioned generally opposite the hard stop 180. When the third hub portion 130 is proximally retracted from the distal end 181 to the proximal end 179, the angled region 198 may guide the second protruding portion 135 from the distal portion 183 of the groove 178 to the proximal portion 177 of the groove in a single fluid movement. For example, the third hub portion 130 may be proximally retracted from the distal end 181 to the proximal end 179 relative to the second hub portion 128 in a single proximal movement, if so desired, without prohibiting travel of the second protruding portion 135 from the distal portion 183 to the proximal portion 177.

A distal portion 129 of the second hub portion 128 may include a groove or recess 188 configured to receive a mating feature disposed on the first hub portion 126. This may allow the first hub portion 126 to be proximally retracted over the second hub portion 128, as will be discussed in more detail below. The proximal and distal portions 127, 129 of the second hub portion 128 may be separated by a gripping region 176 configured to provide a region for the clinician to hold.

Figure 10A:
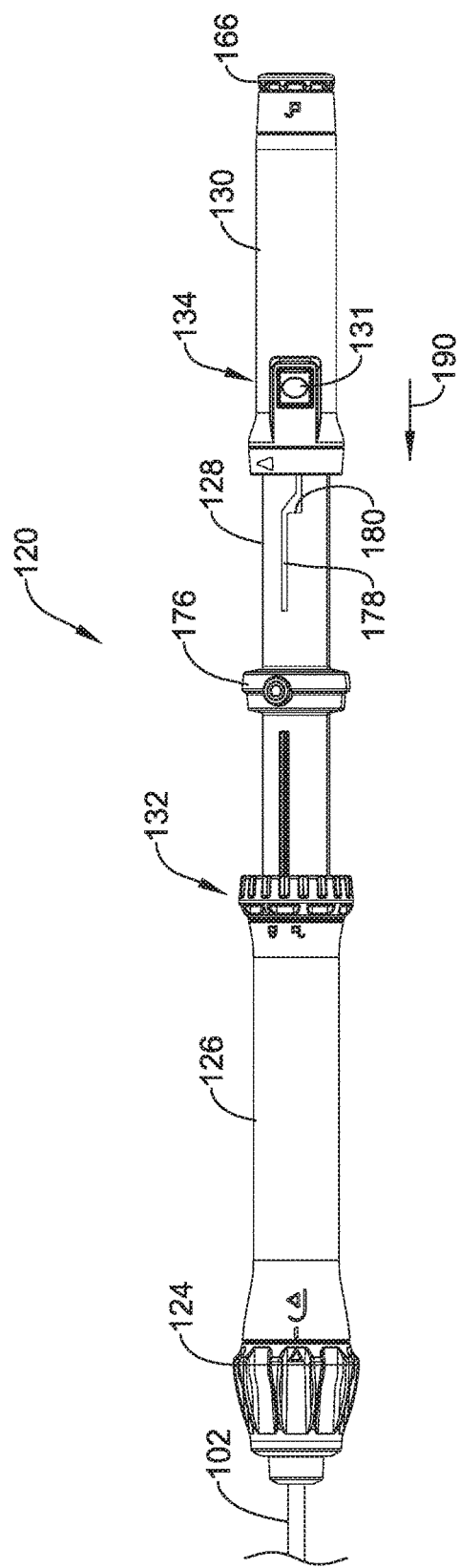
FIGS. 10A-10E are schematic views illustrating the use of the illustrative delivery device to deploy an implantable leadless cardiac pacing device.
Figure 10B:
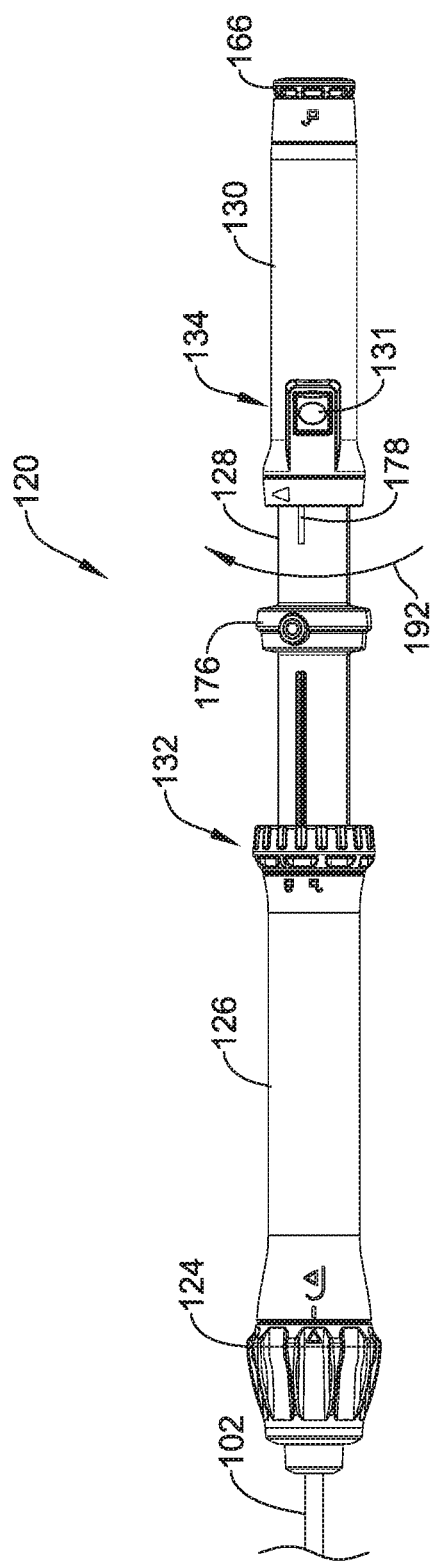

Referring now to FIGS. 10A-10E, a method for deploying a device 10 using the illustrative delivery device 100 will now be described. The delivery device 100 may be introduced into the vasculature through the femoral vein through a previously introduced guide catheter. This is just an example. The delivery device 100 may be introduced through any desired location and with or without the use of a guide catheter as desired. The delivery device 100 may be advanced through the vasculature to the desired treatment location, which, in the case of a leadless cardiac pacing device, may be a chamber of the heart. The clinician may use the actuation mechanism 122 may to deflect the distal end portion 106 of the outer tubular member 102 in a desired manner to facilitate advancement of the delivery device 100. During advancement of the delivery device 100, the handle assembly 120 may be in a fully extended configuration, as shown in FIG. 10A. In such a configuration, the third hub portion 130 may be at its proximal-most location relative to the second hub portion 128 and the first hub portion 126 may be at its distal-most location relative to the second hub portion 128. When the handle assembly 120 is in its fully extending configuration, the inner tubular member 116, intermediate tubular member 110, and the outer tubular member 102 may be oriented in the manner illustrated in FIG. 5. The delivery device 100 can be imaged using known techniques to ensure accurate placement of the device 10.

Figure 10C:
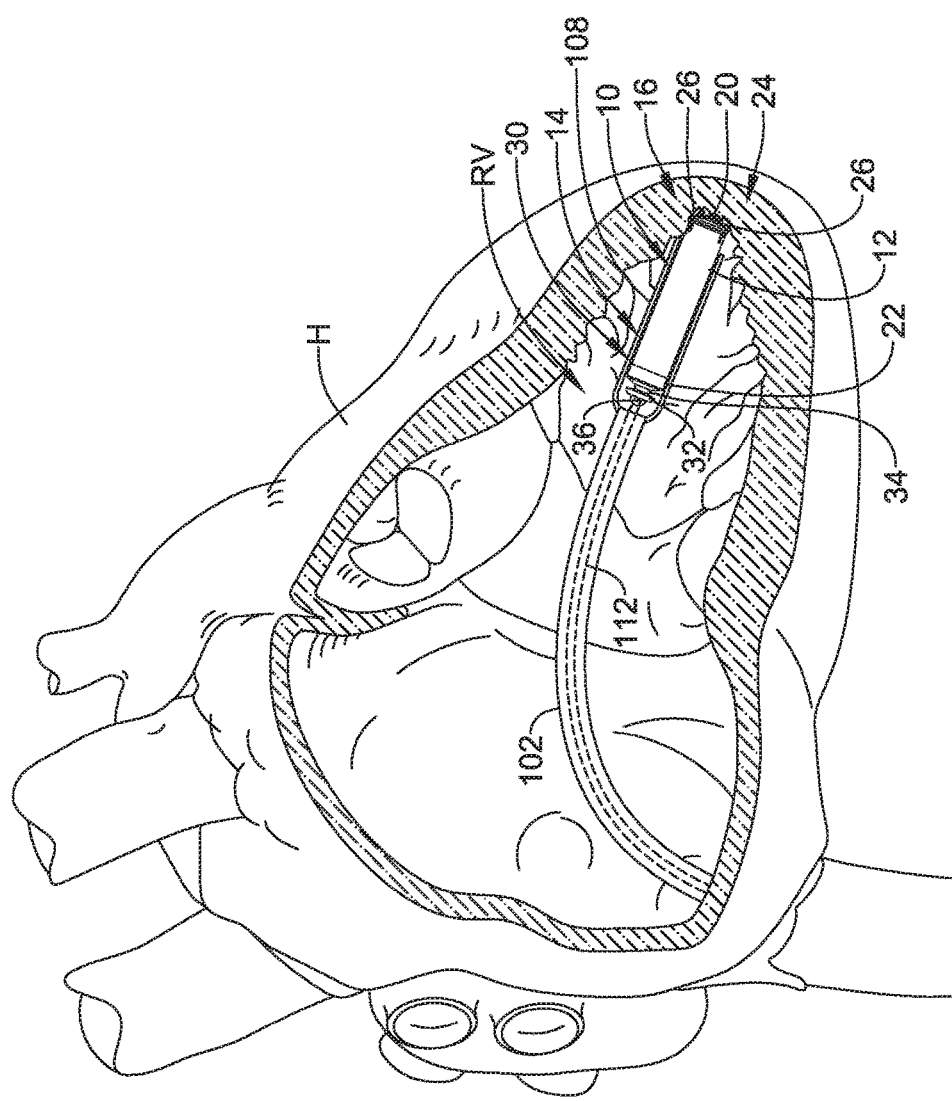
Figure 10D:
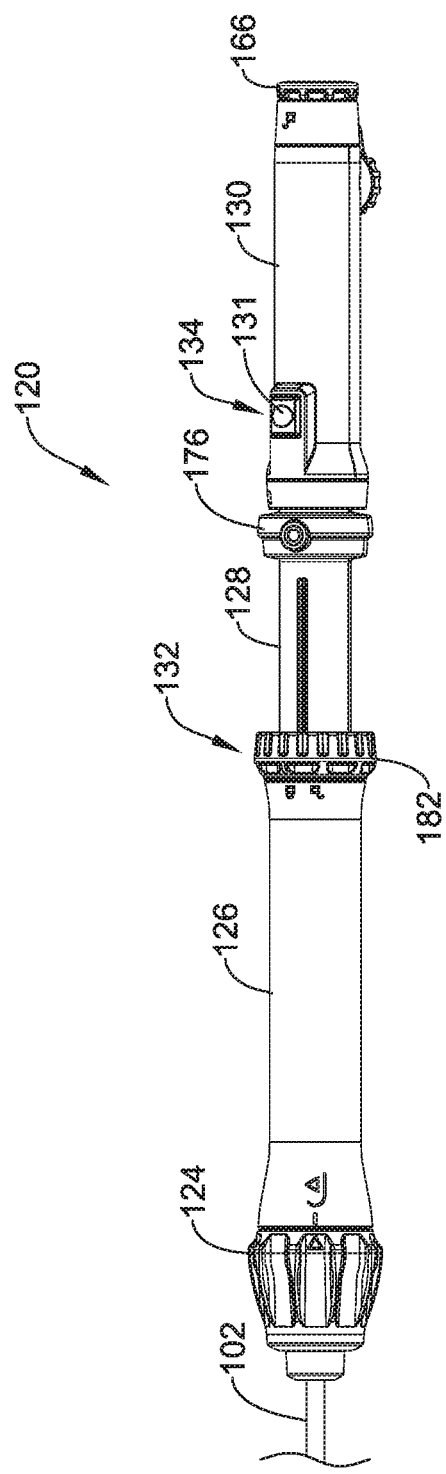

Once the distal tip portion 140 of the distal holding section 108 has been positioned adjacent to the cardiac tissue where the device 10 is desired, deployment of the device 10 can begin. The first stage of the deployment of the device 10 may enable activation of the fixation mechanism 24. To initiate the first stage of deployment, the clinician may stabilize the first hub portion 126 relative to the patient and depress the button 131 of the first locking mechanism 134. The clinician may then slide the third hub portion 130 distally, as shown at 190, until the first locking mechanism 134 engages the hard stop 180 provided in the second hub portion 128 resulting in the handle assembly 120 configuration shown in FIG. 10B. Distal actuation of the third hub portion 130 may also move the inner tubular member 116 distally by the same distance. As the inner tubular member 116 advances distally, the distal end region 118 may "push" against the proximal end 14 of the device 10. As the device 10 is pushed distally, the hooks 26 engage the heart tissue as shown in FIG. 10C. The device 10 may be distally advanced out of the distal holding section 108 to deploy the hooks or tines 26 from the distal holding section 108 to engage the hooks or tines 26 in the heart tissue while the proximal portion of the device 10 remains within the distal holding section 108. In some instances, the device 10 may be advanced distally in the range of 1 to 5 millimeters, although other distances are contemplated. This may allow the device 10 to be deployed while minimizing the amount of pressure applied to the heart wall. Further, the first locking mechanism 134 may prevent accidental or unintentional deployment of the device 10 as the button 131 must be actuated while advancing the third hub portion 130.

Figure 11A:
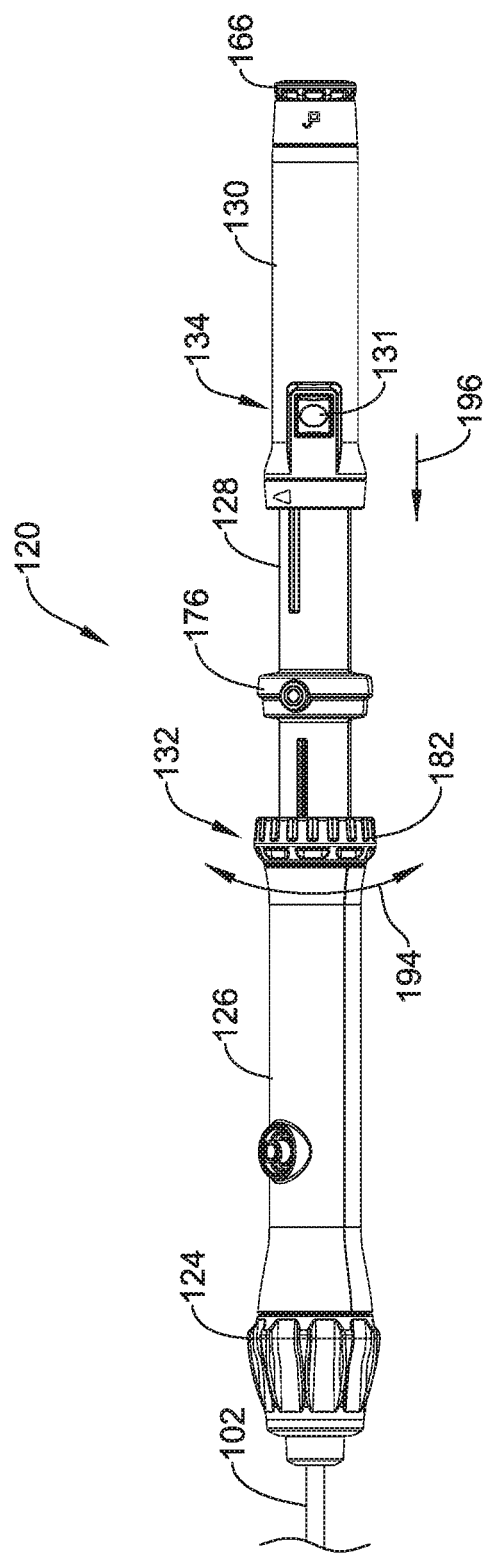
FIGS. 11A-11B are schematic views illustrating a telescoping feature of the illustrative delivery device.
Figure 11B:
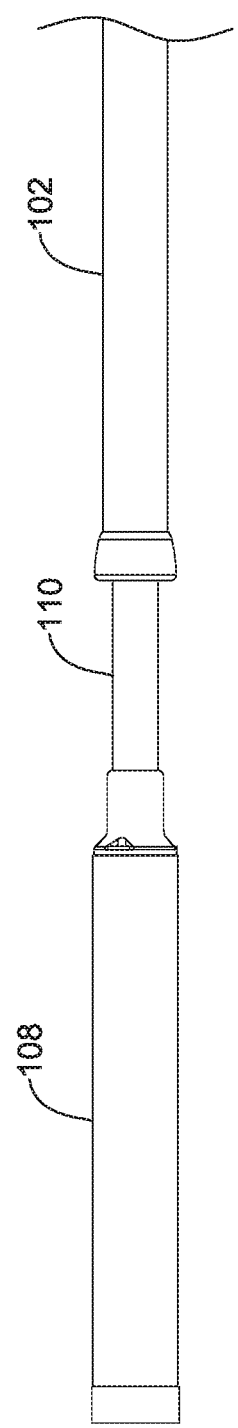

Referring briefly to FIGS. 11A and 11B, in some instances, it may be desirable to advance the distal holding section 108 and the intermediate tubular member 110 without advancing the outer tubular member 102 (i.e., telescoping the intermediate tubular member 110). For example, this may facilitate advancement of the delivery device 100 within the heart or maintain the position of the distal holding section 108 once it is placed again the heart wall. To distally advance or telescope the intermediate tubular member 110 relative to the outer tubular member 102, the second locking mechanism 132 may be actuated to "unlock" the first hub portion 126 and the second hub portion 128. As described above, a rotating retaining ring 182 may be rotated, as shown at 194, to move the second locking mechanism 132 from a locked to an unlocked configuration. Once the first locking mechanism has been unlocked, the clinician may distally advance 196 the second and third hub portions 128, 130 together to distally advance the distal holding section 108 as far as desired and/or needed. The actuation of the second and third hub portions 128, 130 may simultaneously move the intermediate tubular member 110 and the inner tubular member 116 as well. This may be done during advancement of the delivery device 100 through the vasculature, before initiating the first stage of device 10 deployment, and/or after the first stage of device 10 deployment has been completed, as desired or needed.

After the first stage of deployment of the device 10, in which the tines or hooks 26 have been deployed from the distal holding section 108 into engagement with the heart wall, the tether 112 may be used to perform a tug test to determine if the device 10 is sufficiently engaged with the heart wall. In other words, the fixation of the device 10 (e.g. how well the hooks 26 are secured to the heart tissue) may be tested by gently tugging on the ends of the tether 112. If it is determined that the device 10 is sufficiently engaged with the heart wall, then the user may proceed to the second stage of deployment of the device 10 in which the remainder of the device 10 is expelled from the distal holding section 108. Otherwise, if the tug test fails and it is determined that the device 10 is not sufficiently engaged with the heart wall, the user may use the tether to pull (retract) the device 10, including the tines or hooks 26, back into the distal holding section 108 to release the device 10 from the heart wall. The device 10 may then be repositioned and the first stage of deployment repeated.

Returning to FIG. 10B, the second stage of the deployment of the device 10 may proximally retract the distal holding section 108, and thus the intermediate tubular member 110, relative to the inner tubular member 116 to fully deploy the device 10. Once the clinician has determined that the position of the device 10 is satisfactory and the fixation mechanism 24 is securely engaged with the heart tissue, the intermediate tubular member 110, including the distal holding section 108, of the delivery device 100 can be proximally retracted. To initiate the second stage of the deployment, the clinician may first rotate the third hub portion 130, as shown at 192, such that the button 131 is aligned with the distal portion 183 of the groove 178. The clinician may then stabilize the third hub portion 130 relative to the patient and proximally retract the first and second hub portions 126, 128. It should be noted that while it is possible to distally actuate the third hub portion 130 at this point, this may cause additional and unnecessary forces to be applied to the heart wall. Further, such distal movement of the third hub portion 130 may move the inner tubular member 116 (and hence device 10) distally rather than proximally retracting the intermediate tubular member 110 and/or the outer tubular member 102. The first and second hub portions 126, 128 may be proximally retracted until the first locking mechanism 134 engages the distal end 181 of the groove 178, resulting in the handle assembly 120 configuration shown in FIG. 10D. Such actuation of the first and second hub portions 126, 128 may fully deploy the device 10 such that the device 10 is exterior of the distal holding section 108 and engaged with the heart wall, as shown in FIG. 10E.

Figure 10E:
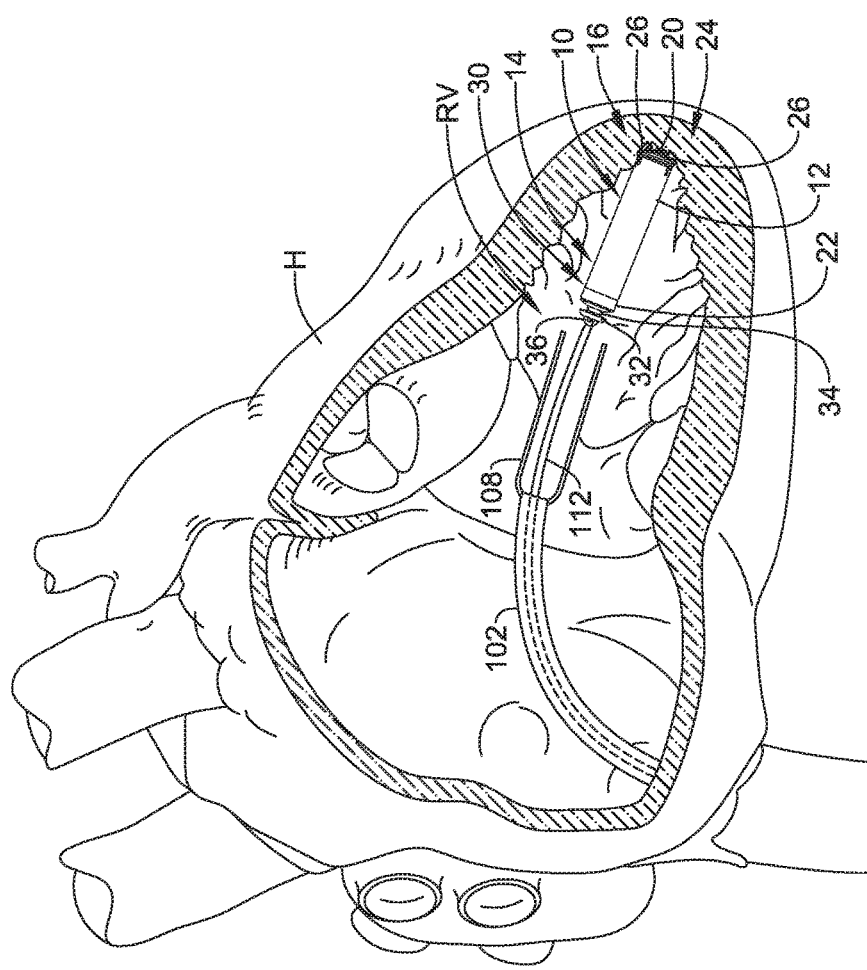

As can be seen in FIG. 10E, the device 10 may still be affixed to the delivery device 100 through the tether 112. Once the clinician has verified the position of the device 10, the fixation of the device 10 and/or the electrical performance of the device 10, the tether 112 may be removed. It is contemplated that the fixation of the device 10 (e.g. how well the hooks 26 are secured to the heart tissue) may be tested by gently tugging on the ends of the tether 112. The tether 112 may be removed by unlocking the tether lock 164, removing the tether cap 166, cutting the tether 112 at some location along its length, and pulling on one of the ends until the opposite end has passed through the opening 38 of the device 10 such that the device 10 is free from the tether 112.

In some instances, the tether 112 may be affixed to a portion of the tether cap 166 (e.g. creating a loop) such that the tether 112 must be cut to allow the device 10 to be freed from the tether 112.

The materials that can be used for the various components of the delivery devices, such as delivery device 100 (and/or other delivery structures disclosed herein) and the various members disclosed herein may include those commonly associated with medical devices. For simplicity purposes, the following discussion makes reference the delivery device 100 and components of thereof. However, this is not intended to limit the devices and methods described herein, as the discussion may be applied to other similar delivery systems and/or components of delivery systems or devices disclosed herein.

The delivery device 100 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A delivery system for delivering an implantable leadless pacing device, the delivery system comprising:
    a delivery device, the delivery device comprising:
        a tubular member including a lumen extending from a proximal end to a distal end thereof, the tubular member including a distal holding section defining a cavity therein; and
        a handle assembly;
    an implantable leadless pacing device configured to be disposed within the cavity of the distal holding section, the leadless pacing device comprising:
        a housing having a proximal end and a distal end;
        a fixation mechanism disposed adjacent the distal end; and
        a tether retention feature disposed adjacent to the proximal end; and
    a tether configured to releasably secure the implantable leadless pacing device to the delivery device, the tether releasably coupled to the tether retention feature of the leadless pacing device and extending to the handle assembly of the delivery device;
    the tether consisting of a multifilament of ultra-high-molecular-weight polyethylene (UHMWPE) material extending from a first terminal end of the tether to a second terminal end of the tether, the UHMWPE material having a tensile strength in the range of 26.7 Newtons (N) to 89.0 N.

2. The delivery system of claim 1, wherein the UHMWPE material has a tensile strength in the range of 35.6 N to 44.5 N.

3. The delivery system of claim 1, wherein the UHMWPE material has a modulus of elasticity in the range of 96.5 gigapascals (GPa) to 131 GPa.

4. The delivery system of claim 1, wherein the UHMWPE material has a coefficient of friction of less than 0.05.

5. The delivery system of claim 1, wherein handle assembly includes a proximal hub portion, an intermediate hub portion, and a distal hub portion arranged in a telescoping arrangement such that the distal hub portion is longitudinally slidable relative to the intermediate hub portion and the proximal hub portion is longitudinally slidable relative to the intermediate hub portion;
    wherein the intermediate hub portion extends distal of a distal end of the proximal hub portion and the distal hub portion extends distal of a distal end of the intermediate hub portion.

6. The delivery system of claim 5, wherein the distal end of the proximal hub portion surrounds a proximal end of the intermediate hub portion and a proximal end of the distal hub portion surrounds the distal end of the intermediate hub portion.

7. A delivery system for delivering an implantable leadless pacing device, the delivery system comprising;
    a delivery device, the delivery device comprising:
        an outer tubular member including a lumen extending, from a proximal end to a distal end thereof;
        an intermediate tubular member slidably disposed in the lumen of the outer tubular member, the intermediate tubular member including a lumen extending from a proximal end to a distal end thereof, the intermediate tubular member including a distal holding section positioned distal of the distal end of the outer tubular member, the distal holding section defining a cavity therein;
        an inner tubular member slidably disposed in the lumen of the intermediate tubular member, the inner tubular member including a lumen extending from a proximal end to a distal end thereof; and
        a handle assembly including a distal hub portion affixed to the proximal end of the outer tubular member, an intermediate hub portion affixed to the proximal end of the intermediate tubular member, and a proximal hub portion affixed to the proximal end of the inner tubular member,
        wherein the intermediate hub portion extends distal of a distal end of the proximal hub portion and the distal hub portion extends distal of a distal end of the intermediate hub portion;
        wherein the distal hub portion, the intermediate hub portion and the proximal hub portion are in a telescoping arrangement such that the distal hub portion is longitudinally slidable relative to the intermediate hub portion to move the intermediate tubular member relative to the outer tubular member, the proximal hub portion is longitudinally slidable relative to the intermediate hub portion to move the inner tubular member relative to the intermediate tubular member;
    an implantable leadless pacing device configured to be disposed within the cavity of the distal holding section, the leadless pacing device comprising:
        a housing having a proximal end and a distal end;
        a fixation mechanism disposed adjacent the distal end; and
        a docking member comprising a tether retention loop disposed adjacent to the proximal end; and
    a tether comprising a length of material having a first end and a second end and configured to releasably secure the implantable leadless pacing device to the delivery device, the tether looped around the tether retention loop and extending through the lumen of the inner tubular member to a proximal end of the proximal hub portion of the handle assembly of the delivery device.

8. The delivery system of claim 7, wherein the tether has a tensile strength in the range of 35.6 Newtons (N) to 44.5 N.

9. The delivery system of claim 7, wherein the tether has a modulus of elasticity in the range of 96.5 gigapascals (GPa) to 131 GPa.

10. The delivery system of claim 7, wherein the tether has a coefficient of friction of less than 0.05.

11. The delivery system of claim 7, wherein the tether comprises a monofilament ultra-high-molecular-weight polyethylene (UHMWPE).

12. The delivery system of claim 7, wherein the tether comprises a multifilament UHMWPE.

13. The delivery system of claim 7, wherein the tether comprises a monofilament polyether ether ketone (PEEK).

14. The delivery system of claim 7, wherein the tether comprises a polytetrafluoroethylene (PTFE) coated nitinol wire or cable.

15. The delivery system of claim 7, wherein the tether comprises an ethylene tetrafluoroethylene (ETFE) coated nitinol wire or cable.

16. A delivery system for delivering an implantable leadless pacing device, the delivery system comprising:
a delivery device, the delivery device comprising:
a tubular member including a lumen extending from a proximal end to a distal end thereof, the tubular member including a distal holding section defining a cavity therein;
a pusher member extending through the lumen of the tubular member; and
a handle assembly configured to actuate the pusher member relative to the tubular member;
an implantable leadless pacing device configured to be disposed within the cavity of the distal holding section, the leadless pacing device comprising:
a housing having a proximal end and a distal end;
a fixation mechanism disposed adjacent the distal end; and
a docking member comprising a tether retention loop disposed adjacent to the proximal end; and
a tether consisting of a length of material having a first end at a first terminal end of the tether and a second end at a second terminal end of the tether and configured to releasably secure the implantable leadless pacing device to the delivery device, the tether looped around the tether retention loop and extending to the handle assembly of the delivery device;
wherein the material forming the tether has a tensile strength in the range of 35.6 Newtons (N) to 44.5 N, a modulus of elasticity in the range of 96.5 gigapascals (GPa) to 131 GPa, and a coefficient of friction of less than 0.05.

17. The delivery system of claim 7, wherein the first and second ends of the tether are secured to a tether cap, wherein the tether cap is removably secured to a proximal end of the proximal hub portion.

18. The delivery system of claim 17, wherein the handle assembly includes a tether lock actuatable between a locked configuration and an unlocked configuration.

19. The delivery system of claim 18, wherein the tether lock includes a port in fluid communication with the lumen of the inner tubular member.

20. The delivery system of claim 18, wherein the distal end of the proximal hub portion surrounds a proximal end of the intermediate hub portion and a proximal end of the distal hub portion surrounds the distal end of the intermediate hub portion.

* * * * *